United States Patent
Shen et al.

(10) Patent No.: US 6,921,734 B2
(45) Date of Patent: Jul. 26, 2005

(54) TITANOCENE COMPLEXES AND ITS CATALYST FOR PREPARING SYNDIOTACTIC POLYSTYRENE

(75) Inventors: Zhigang Shen, Shanghai (CN); Shang'an Lin, Shangai (CN); Wenle Zhou, Shanghai (CN); Fangming Zhu, Shanghai (CN); Huiming Zhang, Shanghai (CN); Zaiku Xie, Shanghai (CN)

(73) Assignees: China Petroleum & Chemical Corporation, Beijing (CN); Shanghai Research Institute of Petrochemical Tech., Shanghai (CN)

( * ) Notice: Subject to any disclaimer, the term of this patent is extended or adjusted under 35 U.S.C. 154(b) by 141 days.

(21) Appl. No.: 10/410,036

(22) Filed: Apr. 9, 2003

(65) Prior Publication Data

US 2004/0023794 A1 Feb. 5, 2004

(30) Foreign Application Priority Data

| Apr. 10, 2002 | (CN) | 02111301 A |
| Apr. 10, 2002 | (CN) | 02111302 A |
| Jul. 10, 2002 | (CN) | 02112446 A |
| Jul. 10, 2002 | (CN) | 02112447 A |
| Jul. 10, 2002 | (CN) | 02112448 A |
| Jul. 10, 2002 | (CN) | 02112449 A |

(51) Int. Cl.[7] ............... B01J 31/00; B01J 37/00; C08F 4/02; C08F 4/60

(52) U.S. Cl. ............... 502/103; 502/110; 502/114
(58) Field of Search ............... 502/103, 110, 502/114

(56) References Cited

U.S. PATENT DOCUMENTS

| 4,978,730 A | 12/1990 | Maezawa et al. |
| 5,023,222 A | 6/1991 | Maezawa et al. |
| 5,045,517 A | 9/1991 | Campbell, Jr. et al. |
| 5,196,490 A | 3/1993 | Campbell, Jr. et al. |
| 5,252,693 A | 10/1993 | Ishihara et al. |
| 5,596,054 A * | 1/1997 | Takeuchi ............... 526/134 |
| 6,342,463 B1 * | 1/2002 | Stephan et al. ............... 502/103 |

FOREIGN PATENT DOCUMENTS

EP 0210615 A2 4/1987

* cited by examiner

*Primary Examiner*—J. A. Lorengo
*Assistant Examiner*—J. Pasterczyk
(74) *Attorney, Agent, or Firm*—Cohen, Pontani, Lieberman & Pavane

(57) ABSTRACT

The present invention relates to a titanocene complex and a catalyst comprising the same and an alkylaluminoxane for preparing syndiotactic polystyrene. The catalyst is applicable to the industrial production of the syndiotactic polymerization of styrene. The titanocene complex has a general formula of $R_1Ti(OR_2R_3)_3$, where $R_1$ is Cp or Cp containing 1–5 $C_{1-4}$ alkyls, $R_2$ is an aryl containing 6–12 carbon atoms, $R_3$ is a halogen, $OR_2R_3$ is a halogenated aryloxy ligand.

8 Claims, No Drawings

TITANOCENE COMPLEXES AND ITS CATALYST FOR PREPARING SYNDIOTACTIC POLYSTYRENE

FIELD OF THE INVENTION

The present invention relates to titanocene complexes and their catalysts for preparing syndiotactic polystyrene.

DESCRIPTION OF THE RELATED ART

When a homogeneously catalytic system consisting of titanocene complexes and a promoter, methylaluminoxyl (MAO), or a boron-fluorine compound is used in the syndiotactic polymerization of styrene, a syndiotactic polymer with a syndiotactic degree of higher than 96% can be obtained. The melting point of the polymer is as high as 270° C. and it has the advantages of a high crystallization speed, good chemicals resistance, good thermal resistance, narrow molecular weight distribution, good dimension stability, excellent electric performance, and comprehensive performance comparable to engineering plastics. The appearance of syndiotactic polystyrene (SPS) has initiated the study on the catalytic system, especially the main catalyst, metallocene compounds. U.S. Pat. No. 5,252,693 and EP210615 report the application of the catalytic system consisting of $CpTiCl_3$ or $Cp^*TiCl_3$, and the promoter, MAO, in the syndiotactic polymerization of styrene, wherein Cp is cyclopentadienyl and Cp* is pentamethyl cyclopentadienyl, but their catalytic activity and catalytic efficiency are not high, and the stability is poor, so they have less value for the industry. U.S. Pat. No. 4,978,730, U.S. Pat. No. 5,023,222, U.S. Pat. No. 5,045,517, and U.S. Pat. No. 5,196,490 report the $CpTi(OR)_3$ and $Cp^*Ti(OR)_3$ type catalysts having higher activity nowadays. Although their activity is higher than before, they are mostly viscous liquid and troublesome to purify and store.

SUMMARY OF THE INVENTION

The first technical problem to be solved by the present invention is overcoming the problem in the prior art that the catalytic activity of the titanocene complexes is far from the requirement of industrialization by providing a new titanocene complex. This compound has the characters of good thermal stability at 90° C., being a solid at normal temperature, ease to purify, and less drop in activity after a long term of storage. The second technical problem to be solved by the present invention is overcoming the problem present in the prior art of low activity in preparing syndiotactic polystyrene by providing a new catalyst for preparing syndiotactic polystyrene. This catalyst has the character of higher catalytic activity.

To solve the aforesaid first problem, the solution adopted by the present invention is as follows: titanocene complexes, which have the following general formula:
$R_1Ti(OR_2R_3)_3$
where $R_1$ is cyclopentadienyl or cyclopentadienyl containing 1–5 $C_{1-4}$ alkyls;
$R_2$ is an aryl containing 6–12 carbon atoms;
$R_3$ is a halogen;
wherein there is an oxygen atom between Ti and $R_2$ to connect them.
Preferably, $R_1$ is cyclopentadienyl or pentamethyl cyclopentadienyl, and more preferably, $R_1$ is pentamethyl cyclopentadienyl. Preferably, $R_2$ is an alkaryl containing 6–12 carbon atoms, more preferably, $R_2$ is phenyl, indenyl, or biphenylyl, and most preferably, $R_2$ is phenyl. Preferably, $R_3$ is selected from the group consisting of fluorine, chlorine, bromine, or iodine.

To solve the aforesaid second problem, the solution adopted by the present invention is as follows: a catalyst for preparing syndiotactic polystyrene comprising aforesaid titanocene complexes I and alkylaluminoxyl II:

I

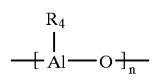

II where $R_1$ is cyclopentadienyl or cyclopentadienyl containing 1–5 $C_{1-4}$ alkyls;
$R_2$ is an aryl containing 6–12 carbon atoms;
$R_3$ is a halogen;
there is an oxygen atom between Ti and $R_2$ to connect them;
$R_4$ is an alkyl containing 1–4 carbon atoms;
n is the oligomerization degree of the alkylaluminoxyl, the value of which is 6–40;
wherein the mole ratio of aluminum in alkylaluminoxyl II to the titanocene complexes I is 50–2000.

Preferably, the oligomerization degree of the alkylaluminoxyl n is in the range between 10 and 30. Preferably, the catalyst also contains triisobutylaluminum and the mole ratio of triisobutylaluminum to alkylaluminoxyl is 0.1–2.

DETAILED DESCRIPTION OF THE PRESENTLY PREFERRED EMBODIMENTS

The process of the present invention for preparing titanocene complexes I is reacting the corresponding cyclopentadienyl titanium trichloride with a corresponding substituted phenol in the presence of a hydrochloride absorbent with a hydrocarbon as the solvent. The hydrochloride absorbent may be various amine compounds, wherein trialkylamine such as triethylamine is more suitable. The hydrocarbon may be aliphatic or aromatic hydrocarbon with aromatic hydrocarbon such as benzene, toluene, xylene, etc being preferred. The mole ratio of cyclopentadienyl titanium trichloride to hydroxyl is 1:3.0–3.5, the mole ratio of cyclopentadienyl titanium trichloride to triethylamine is 1:3.0–4.0, the reaction temperature is 1–130° C., preferably 30–80° C., the reaction time is 2–48 h, preferably 6–24 h, the reaction course is preferably the batch heating operation. The solid is removed by filtration under the protection of an inert gas and the solvent is removed by vacuum distillation. The derived raw product is extracted with hexane yielding a crystal after removing the volatile substance.

Polyalkylaluminoxyl is prepared by controlled hydrolysis of alkylaluminum. The reactant water may be the water in the inorganic salts containing crystallization water and the inorganic salts containing crystallization water may be $CaCl_2 \cdot 6H_2O$, $MgCl_2 \cdot 6H_2O$, $CuSO_4 \cdot 5H_2O$, $CaSO_4 \cdot 2H_2O$, $Al_2(SO_4)_3 \cdot 18H_2O$, $MgSO_4 \cdot 7H_2O$, $FeSO_4 \cdot 7H_2O$, $Ti(SO_4)_2 \cdot 4H_2O$, $Ti_2(SO_4)_3 \cdot 8H_2O$ and $ZnSO_4 \cdot 7H_2O$, etc. The mole ratio of trimethylaluminum (TMA) to water is 1:1–1:3, reaction temperature is −20~100° C., reaction time is 10–40 h. The commonly used alkylaluminum includes trimethylaluminum, triethylaluminum, and triisobutylaluminum. The specific procedure is slowly dropping the alkylaluminum into a mixed solution of $Al_2(SO_4)_3 \cdot 18H_2O$ in toluene in an $Al/H_2O$ mole ratio of 1:1–1:2 at −20~0° C. in 0.5–4 h. Then the temperature is gradually raised to 20–100° C. and the reaction continues at this temperature for 5–40 h. The solid is removed from the reaction mixture under the protection of an inert gas by filtration and the solvent is vaporized in vacuum, yielding a white solid product, i.e. the alkylaluminoxyl with structure II.

The structure of the compound is as follows when $R_1$ is pentamethyl cyclopentadienyl, $R_2$ is phenyl, and $R_3$ is para-fluorine:

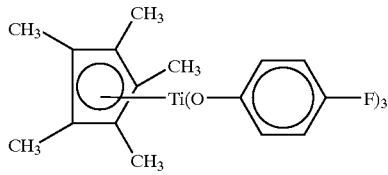

The analytical data are as follows:
Element analysis
$C_{28}H_{27}O_3F_3Ti$:
Calcd. For
  C 65.11%
  H 5.23%
  F 11.04%
Found
  C 65.06%
  H 5.30%
  F 10.97%
Nuclear magnetic resonance spectra of hydrogen nucleus [HNMR CDCl$_3$ TMS intern]
δ 6.55–7.00 (m, 12H, -(OPhHF)$_3$)
δ 2.0–2.15 (s, 15H, Cp-CH$_3$)
Mass spectroscopy analysis MS (m/e, % intensity)
516 (36.99, M)
517 (43.13, M+1)
406 (100, M-OPhF)

When $R_1$ is pentamethyl cyclopentadienyl, $R_2$ is phenyl, and $R_3$ is para-chlorine, the structure of the compound is:

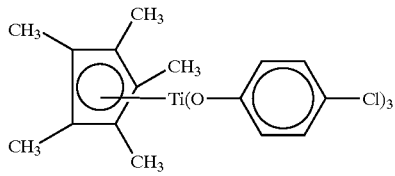

The analytical data are as follows:
Element analysis
$C_{28}H_{27}O_3Cl_3Ti$:
Calcd. For
  C 59.42%
  H 4.77%
  Cl 18.83%
Found
  C 59.25%
  H 4.79%
  Cl 18.71%
Nuclear magnetic resonance spectra of hydrogen nucleus [HNMR CDCl$_3$ TMS intern]
δ 6.75–7.25 (m, 12H, -(OPhHCl)$_3$)
δ 1.90–2.15 (s, 15H, Cp-CH$_3$)
Mass spectroscopy analysis MS (m/e, % intensity)
566 (32.18, M)
567 (41.25, M+1)
438 (100, M-OPhCl)

When $R_1$ is pentamethyl cyclopentadienyl, $R_2$ is phenyl, and $R_3$ is para-bromine, the structure of the compound is:

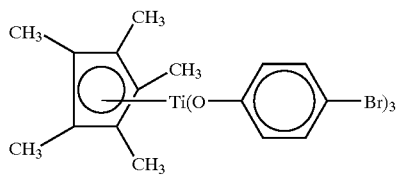

The analytical data are as follows:
Element analysis
$C_{28}H_{27}O_3Br_3Ti$:
Calcd. For
  C 48.07%
  H 3.86%
  Br 18.83%
Found
  C 48.16%
  H 4.13%
  Br 17.71%
Nuclear magnetic resonance spectra of hydrogen nucleus [HNMR CDCl$_3$ TMS intern]
δ 6.55–7.35 (m, 12H, -(OPhHBr)$_3$)
δ 1.9–2.15 (s, 15H, Cp-CH$_3$)
Mass spectroscopy analysis MS (m/e, % intensity)
699 (37.75, M)
700 (34.15, M+1)
527 (100, M-OPhBr)

When $R_1$ is pentamethyl cyclopentadienyl, $R_2$ is phenyl, and $R_3$ is para-iodine, the structure of the compound is:

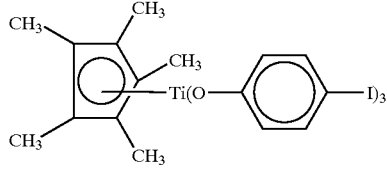

The analytical data are as follows:
Element analysis
$C_{28}H_{27}O_3I_3Ti$:
Calcd. For
  C 40.00%
  H 3.21%
  I 45.36%
Found
  C 40.12%
  H 3.47%
  I 44.10%
Nuclear magnetic resonance spectra of hydrogen nucleus [HNMR CDCl$_3$ TMS intern]
δ 6.55–7.50 (m, 12H, -(OPhHI)$_3$)
δ 2.0–2.15 (s, 15H, Cp-CH$_3$)
Mass spectroscopy analysis MS (m/e, % intensity)
840 (8.92, M)
841 (3.72, M+1)
220 (100, -OPhI)
621 (24.44%, M-OPhI)

Catalyst component I may first reacts with catalyst component II at 0–50° C., preferably 30° C. under the protection of an inert gas (such as nitrogen, argon, etc).

The polymerization reaction proceeds at 30–100° C., preferably 60–90° C. In order to obtain a polymer with ideal performance, it should last a certain time, e.g. from several minutes to several hours, preferably from 0.1 to 3 h. The ideal polymerization time depends on the polymerization temperature, solvent and other polymerization conditions. The mode of the polymerization reaction may adopt solution polymerization, slurry polymerization, and bulk polymerization. For solution polymerization and slurry polymerization, the adopted solvent is aliphatic or aromatic hydrocarbons such as hexane, heptane, cyclohexane, benzene, toluene, etc. The concentration of styrene in the solvent is 5–100%.

When the present invention uses a new titanocene complex as a main catalyst for preparing syndiotactic polystyrene, and the compound together with alkylaluminoxyl or/and triisobutylaluminum are used as the catalyst for preparing syndiotactic polystyrene, the efficiency of the catalyst can attain 523 kg polymer/gTi at most, a better result.

The present invention will be further illustrated below by examples.

EXAMPLES

Example 1

Preparation of the Titanocene Fluorine Complexes
(A)

A 250 ml dry three-necked bottle was purged with $N_2$ for three times, whereto 1.317 g of pentamethyl trichloromonocyclopentadienyl titanium and 90 ml of benzene were added and a mixture of 30 ml of benzene, 1.53 g of parafluorophenol, and 1.38 g of triethylamine was dropped from the top in 30 min. After reacting at room temperature for 1 h, the content was heated to the reflux temperature of benzene. After reacting for 2 h, heating was stopped and the reaction was conducted at room temperature for 16 h. The content was filtered and the filtrate was evacuated for drying. The derived solid was repeatedly recrystallized for three times with a mixed solution of toluene and hexane (1:10) and evacuated for drying, yielding 1.97 g of light yellow crystal with a yield of 84%.

Example 2

Preparation of the Titanocene Chlorine Complexes
(B)

A 250 ml dry three-necked bottle was purged with $N_2$ for three times, whereto 1.016 g of pentamethyl trichloromonocyclopentadienyl titanium and 70 ml of benzene were added and a mixture of 30 ml of benzene, 1.35 g of parachlorophenol, and 1.1 g of triethylamine was dropped from the top in 45 min. After reacting at room temperature for 1 h, the content was heated to the reflux temperature of benzene. After reacting for 2 h, heating was stopped and the reaction was conducted at room temperature for 10 h. The content was heated and reacted for 2 h again and then filtered, and the filtrate was evacuated for drying. The derived solid was repeatedly recrystallized with a mixed solution of toluene and hexane and evacuated for drying, yielding 1.74 g of light yellow crystal with a yield of 88%.

Example 3

Preparation of the Titanocene Bromine Complexes
(C)

A 250 ml dry three-necked bottle was purged with $N_2$ for three times, whereto 1.66 g of pentamethyl trichloromonocyclopentadienyl titanium and 95 ml of benzene were added and a mixture of 45 ml of benzene, 2.97 g of parabrominophenol, and 1.76 g of triethylamine was dropped from the top in 40 min. After reacting at room temperature for 2 h, the content was heated to the reflux temperature of benzene. After reacting for 3 h, heating was stopped and the reaction was conducted at room temperature for 18 h. The content was filtered and the filtrate was evacuated for drying. The derived solid was repeatedly recrystallized for three times with a mixed solution of toluene and hexane (1:6) and evacuated for drying, yielding 3.28 g of yellow crystal with a yield of 82%.

Example 4

Preparation of the Titanocene Iodine Complexes
(D)

A 250 ml dry three-necked bottle was purged with $N_2$ for three times, whereto 1.336 g of pentamethyl trichloromonocyclopentadienyl titanium and 100 ml of benzene were added and a mixture of 40 ml of benzene, 3.04 g of paraiodophenol, and 1.42 g of triethylamine was dropped from the top in 35 min. After reacting at room temperature for 1.5 h, the content was heated to the reflux temperature of benzene. After reacting for 4 h, heating was stopped and the reaction was conducted at room temperature for 14 h. The content was filtered and the filtrate was evacuated for drying. The derived solid was repeatedly recrystallized for three times with a mixed solution of toluene and hexane (1:5) and evacuated for drying, yielding 2.94 g of yellow crystal with a yield of 76%.

Example 5

A 50 ml baked dry two-necked bottle was purged with highly pure $N_2$ for three times, whereto 10 ml of refined styrene monomer was added, and the bottle was placed into an oil bath at 60° C. After stirring the content with a magnetic stirrer for 20 min, 0.4 mmol of triisobutylaluminum, 0.4 mmol of MAO, and 0.001 mmol of the titanocene complexes (A) in Example 1 were injected with an injector. After reacting for 10 min, the reaction was stopped with an ethanol-hydrochloric acid solution. The solid was washed and dried, yielding 4.17 g of powder with an activity of 523 kg polymer/(gTi·h), the polymer had the syndiotactic degree of 97%, Mw of $39 \times 10^4$, and melting point of 272° C.

Example 6

The polymerization conditions were the same as those in Example 5 except that the polymerization temperature was 90° C., catalytic activity was 519 kg polymer/(gTi·h), the polymer had the syndiotactic degree of 97%, Mw was $27 \times 10^4$, and melting point was 271° C.

Example 7

The polymerization conditions were the same as those in Example 5 except that the catalyst was placed in a refrigerator (0–5° C.) for three months, catalytic activity was 504 kg polymer/(gTi·h), the polymer had the syndiotactic degree of 98%, Mw was $26 \times 10^4$, and melting point was 271° C.

Example 8

A 50 ml baked dry two-necked bottle was purged with highly pure $N_2$ for three times, whereto 10 ml of refined styrene monomer was added, and the bottle was placed into an oil bath at 60° C. After stirring the content with a magnetic stirrer for 20 min, 0.4 mmol of triisobutylaluminum, 0.4 mmol of MAO, and 0.001 mmol of the titanocene complexes (B) in Example 2 were injected with an injector. After reacting for 10 min, the reaction was stopped with an ethanol-hydrochloric acid solution. The solid was washed and dried, yielding 4.07 g of powder with an activity of 510 kg polymer/(gTi·h), the polymer had the syndiotactic degree of 96%, and Mw of $37 \times 10^4$.

Example 9

The polymerization conditions were the same as those in Example 8 except that the polymerization temperature was 90° C., catalytic activity was 506 kg polymer/(gTi·h), the polymer had the syndiotactic degree of 98%, Mw was $26 \times 10^4$, and melting point was 272° C.

Example 10

The polymerization conditions were the same as those in Example 8 except that the catalyst was placed in a refrigerator (0–5° C.) for three months, catalytic activity was 497 kg polymer/(gTi·h), the polymer had the syndiotactic degree of 98%, Mw was $27 \times 10^4$, and melting point was 271° C.

Example 11

A 50 ml baked dry two-necked bottle was purged with highly pure $N_2$ for three times, whereto 10 ml of refined styrene monomer was added, and the bottle was placed into an oil bath at 60° C. After stirring the content with a magnetic stirrer for 20 min, 0.4 mmol of triisobutylaluminum, 0.4 mmol of MAO, and 0.001 mmol of the titanocene complexes (C) in Example 3 were injected with an injector. After reacting for 10 min, the reaction was stopped with an ethanol-hydrochloric acid solution. The solid was washed and dried, yielding 3.91 g of powder with an activity of 491 kg polymer/(gTi·h), the polymer had the syndiotactic degree of 96%, Mw of $34 \times 10^4$, and melting point of 270° C.

Example 12

The polymerization conditions were the same as those in Example 11 except that the polymerization temperature was 90° C., catalytic activity was 488 kg polymer/(gTi·h), the polymer had the syndiotactic degree of 98%, Mw was $28 \times 10^4$, and melting point was 271° C.

Example 13

The polymerization conditions were the same as those in Example 11 except that the catalyst was placed in a refrigerator (0–5° C.) for three months, the catalytic activity was 478 kg polymer/(gTi·h), the polymer had the syndiotactic degree of 97%, Mw was $27 \times 10^4$, and melting point was 271° C.

Example 14

A 50 ml baked dry two-necked bottle is purged with highly pure $N_2$ for three times, whereto 10 ml of refined styrene monomer was added, and the bottle was placed into an oil bath at 60° C. After stirring the content with a magnetic stirrer for 20 min, 0.4 mmol of triisobutylaluminum, 0.4 mmol of MAO, and 0.001 mmol of the titanocene complexes (D) in Example 4 were injected with an injector. After reacting for 10 min, the reaction was stopped with an ethanol-hydrochloric acid solution. The solid was washed and dried, yielding 3.80 g of powder with an activity of 478 kg polymer/(gTi·h), the polymer had the syndiotactic degree of 97%, Mw of $38 \times 10^4$, and melting point of 271° C.

Example 15

The polymerization conditions were the same as those in Example 14 except that the polymerization temperature was 90° C., catalytic activity was 475 kg polymer/(gTi·h), the polymer had the syndiotactic degree of 98%, Mw was $29 \times 10^4$, and melting point was 271° C.

Example 16

The polymerization conditions were the same as those in Example 14 except that the catalyst was placed in a refrigerator (0–5° C.) for three months, the catalytic activity was 470 kg polymer/(gTi·h), the polymer had the syndiotactic degree of 98%, Mw was $25 \times 10^4$, and melting point was 271° C.

Comparative Example 1

A 50 ml baked dry two-necked bottle was purged with highly pure $N_2$ for three times, whereto 10 ml of refined styrene monomer was added, and the bottle was placed into an oil bath at 60° C. After stirring the content with a magnetic stirrer for 20 min, 0.4 mmol of triisobutylaluminum, 0.4 mmol of MAO, and 0.001 mmol of titanocene complexes $Cp^*Ti(O-CH_3)_3$ of DOW Corp. were injected with an injector. After reacting for 10 min, the reaction was stopped with an ethanol-hydrochloric acid solution. The solid was washed and dried, yielding 4.17 g of powder with an activity of 453 kg polymer/(gTi·h), the polymer had the syndiotactic degree of 97%, Mw of $41 \times 10^4$, and a melting point of 270° C.

Comparative Example 2

The polymerization conditions were the same as those in Comparative Example 1 except that the polymerization temperature was 90° C., catalytic activity was 367 kg polymer/(gTi·h), the polymer had the syndiotactic degree of 98%, Mw was $25 \times 10^4$, and melting point was 269° C.

Comparative Example 3

The polymerization conditions were the same as those in comparative example 1 except that the catalyst was placed in a refrigerator (0–5° C.) for three months, the catalytic activity was 406 kg polymer/(gTi·h), the polymer had the syndiotactic degree of 98%, Mw was $25 \times 10^4$, and melting point was 271° C.

What we claim is:

1. A catalyst for preparing syndiotactic polystyrene comprising a titanocene complex I and an alkylaluminoxane II:

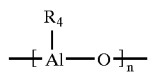

wherein $R_1$ is Cp or Cp containing 1–5 $C_{1-4}$ alkyls;
$R_2$ is an aryl containing 6–12 carbon atoms;
$R_3$ is a halogen;
$OR_2R_3$ is a halogenated aryloxy ligand;

$R_4$ is an alkyl containing 1–4 carbon atoms;

n is the oligomerization degree of the alkylaluminoxane II, the value of which is 6–40; and the mole ratio of aluminum in alkylaluminoxane II to the titanocene complex I is 50–2000.

2. The catalyst of claim 1 wherein the value of the oligomerization degree of the alkylaluminoxane II n is 10–30.

3. The catalyst of claim 1 further comprising triisobutylaluminum, wherein the mole ratio of triisobutylaluminum to alkylaluminoxane II is 0.1–2.

4. The catalyst of claim 1 wherein $R_1$ is Cp or pentamethyl Cp.

5. The catalyst of claim 1 wherein $R_1$ is pentamethyl Cp.

6. The catalyst of claim 1 wherein $R_2$ is alkaryl containing 6–12 carbon atoms.

7. The catalyst of claim 1 wherein $R_2$ is phenyl, indenyl or biphenyl.

8. The catalyst of claim 1 wherein $R_2$ is phenyl.

* * * * *